United States Patent
Lahoda et al.

(10) Patent No.: US 11,289,213 B2
(45) Date of Patent: Mar. 29, 2022

(54) CONTROL RODS FOR LIGHT WATER REACTORS

(71) Applicant: WESTINGHOUSE ELECTRIC COMPANY LLC, Cranberry Township, PA (US)

(72) Inventors: Edward J. Lahoda, Edgewood, PA (US); Frank A. Boylan, Ellwood City, PA (US); Ho Q. Lam, Verona, PA (US); Mitchell E. Nissley, Trafford, PA (US); Raymond E. Schneider, South Windsor, CT (US); Robert L. Oelrich, Columbia, SC (US); Sumit Ray, Columbia, SC (US); Radu Pomirleanu, Wexford, PA (US); Zeses Karoutas, Lexington, SC (US); Michael J. Hone, Prospect, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 609 days.

(21) Appl. No.: 16/051,712

(22) Filed: Aug. 1, 2018

(65) Prior Publication Data
US 2019/0066853 A1 Feb. 28, 2019

Related U.S. Application Data

(60) Provisional application No. 62/552,422, filed on Aug. 31, 2017.

(51) Int. Cl.
G21C 7/24 (2006.01)
G21C 7/10 (2006.01)
(Continued)

(52) U.S. Cl.
CPC .............. *G21C 7/24* (2013.01); *G21C 7/10* (2013.01); *C23C 30/00* (2013.01); *G21C 1/08* (2013.01);
(Continued)

(58) Field of Classification Search
CPC ... G21C 7/24; G21C 7/10; G21C 3/07; G21C 3/328; G21C 7/117; G21C 11/08; G21C 1/08
(Continued)

(56) References Cited

U.S. PATENT DOCUMENTS

| 5,064,607 A | 11/1991 | Miller et al. |
| 5,156,804 A | 10/1992 | Halverson et al. |

(Continued)

FOREIGN PATENT DOCUMENTS

| EP | 0055371 A1 | 7/1982 |
| EP | 0408172 A1 | 1/1991 |

(Continued)

OTHER PUBLICATIONS

IAEA-TECDOC-813, "Advances in control assembly materials for water reactors", Proceedings of a Technical Committee meeting, Vienna 1993. (Year: 1995).*

(Continued)

*Primary Examiner* — Jack W Keith
*Assistant Examiner* — Daniel Wasil
(74) *Attorney, Agent, or Firm* — K&L Gates LLP (57) ABSTRACT

A control rod for a nuclear fuel assembly is described herein that includes a neutron absorbing material having a melting point greater than 1500° C. that does not form a eutectic with a melting point less than 1500° C., and may further include a cladding material having a melting point greater than 1500° C. The cladding material is selected from the group consisting of silicon carbide, zirconium, a zirconium alloy, (Continued)

tungsten, and molybdenum. The absorbing material is selected from the group consisting of $Gd_2O_3$, Ir, $B_4C$, Re, and Hf. The metal cladding or the absorbing material may be coated with an anti-oxidation coating of Cr with or without a Nb intermediate layer.

13 Claims, 2 Drawing Sheets

(51) Int. Cl.
   *G21C 3/07*    (2006.01)
   *G21C 1/08*    (2006.01)
   *G21C 11/08*   (2006.01)
   *G21C 3/328*   (2006.01)
   *C23C 30/00*   (2006.01)

(52) U.S. Cl.
   CPC .............. *G21C 3/07* (2013.01); *G21C 3/328* (2013.01); *G21C 11/08* (2013.01)

(58) Field of Classification Search
   USPC .................... 376/327, 339, 416, 417, 419
   See application file for complete search history.

(56) References Cited

U.S. PATENT DOCUMENTS

| | | |
|---|---|---|
| 8,537,962 B1 | 9/2013 | Drudy et al. |
| 2010/0269960 A1 | 10/2010 | Hertz |

FOREIGN PATENT DOCUMENTS

| | | | |
|---|---|---|---|
| EP | 2088601 B1 | | 10/2012 |
| JP | 2000028774 A | * | 1/2000 |
| JP | 2000028774 A | | 1/2000 |
| JP | 2010216881 A | | 9/2010 |
| JP | 2015206672 A | * | 11/2015 |
| JP | 2015206672 A | | 11/2015 |
| WO | 9748104 A1 | | 12/1997 |
| WO | 2019045970 A1 | | 3/2019 |

OTHER PUBLICATIONS

Supplementary European Search Report for Corresponding European Application Non. EP18852119, dated Jun. 7, 2021.
Domagala et al., The Zirconium-Hafnium System, Journal of the Less-Common Metals (Jul. 1, 1966), 11(1):70-72.
Shibata et al., Evaluation of Neutron Nuclear Data on Hafnium Isotopes for JENDL-4 (Feb. 1, 2010), 47 (2):160-168.
International Search Report and Written Opinion for International PCT Application No. PCT/US2018/045695, dated Feb. 13, 2019.
Supplementary Partial European Search Report for corresponding European Application No. 1885211.9, dated Mar. 24, 2021.

* cited by examiner

CONTROL RODS FOR LIGHT WATER REACTORS

STATEMENT REGARDING GOVERNMENT RIGHTS

This invention was made with government support under Contract No. DE-NE0008222 awarded by the Department of Energy. The U.S. Government has certain rights in this invention.

BACKGROUND OF THE INVENTION

1. Field of the Invention

The invention relates to nuclear reactors, and more specifically, materials for use in making control rods.

2. Description of the Prior Art

Figure 1:
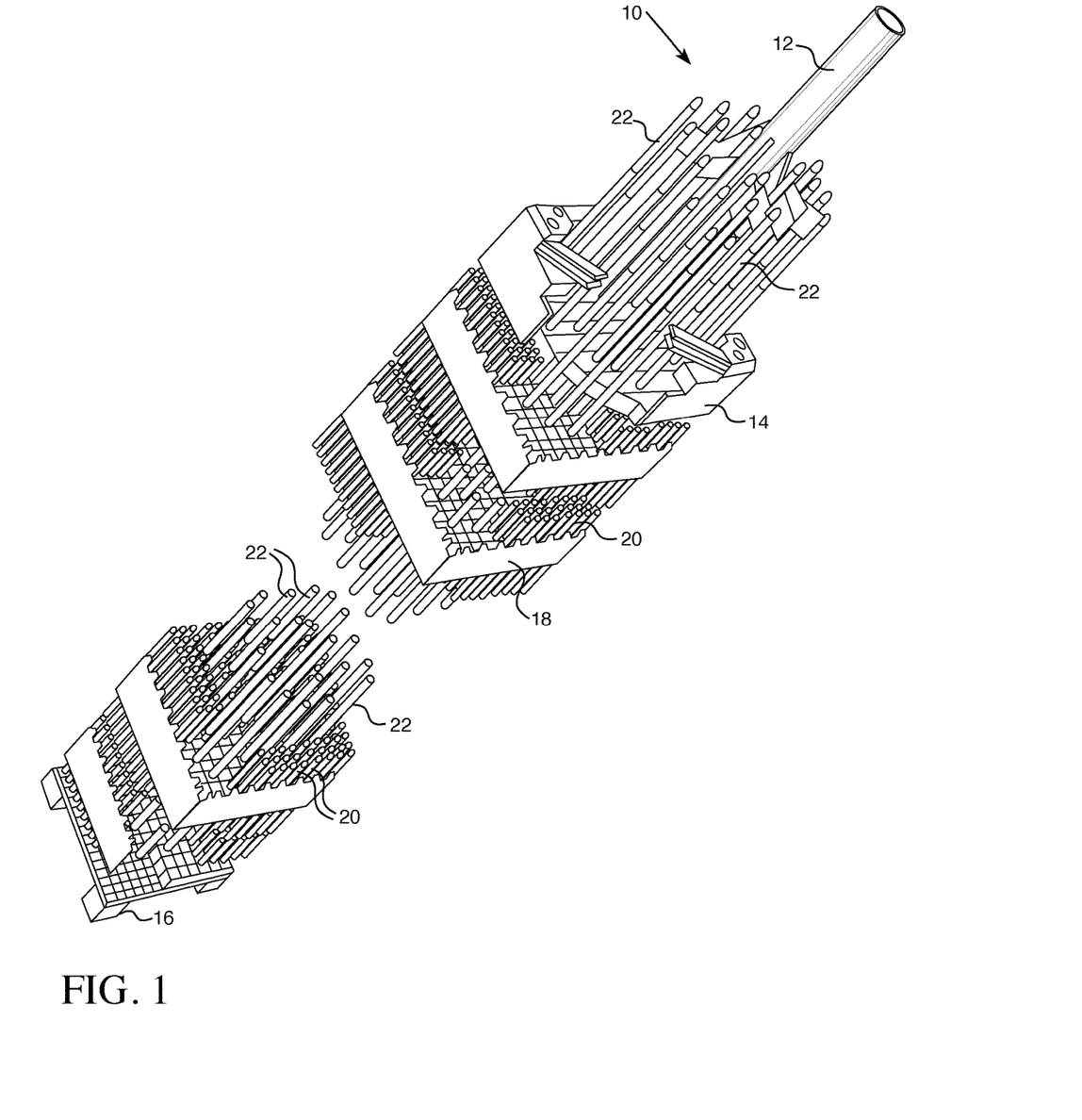
FIG. 1 shows an exemplary conventional fuel rod assembly with a control rod assembly.

In a typical nuclear reactor, the reactor core includes a large number of fuel assemblies, each of which is composed of a plurality of elongated fuel rods or similar elements. Within the array of fuel rods are guide tubes for receiving control rods. Above the assembly of fuel rods is a control rod assembly that includes a number of control rods that, in exemplary designs, can be moved into and out of alignment with the guide tubes positioned among the several fuel rod clusters. FIG. 1 shows an exemplary nuclear fuel assembly, including control rod guide tubes and a rod cluster control assembly.

In use, the control rod assembly is moved as needed and the control rods are dropped into the guide tubes at a strategic position, depending on the operational requirements of the fuel assembly at any given time.

Current control rods, such as those made from Ag—In—Cd alloys in stainless steel cladding, can tolerate and continue to work in environments up to 1168° C. Since the control rods are about 200° C. cooler than the fuel rods and the fuel rods are kept below the current 1200° C. limit for design basis accidents, the current control rod materials are adequate for normal operating conditions. However, in the event of an accident that results in temperature increases beyond those for which the reactor was designed (i.e., beyond design basis accidents), control rod temperatures of about 1700° C. can be reached. At these temperatures, the current control rods would become molten and attack the fuel rods.

Although rare, events such as the tsunami that damaged the nuclear power plants at Fukushima, Japan, demonstrate that beyond design basis accidents can occur and must be accounted for in designing the features of a nuclear power plant. The possibility of a control rod melt down must therefore be addressed.

SUMMARY OF THE INVENTION

The following summary is provided to facilitate an understanding of some of the innovative features unique to the embodiments disclosed and is not intended to be a full description. A full appreciation of the various aspects of the embodiments can be gained by taking the entire specification, claims, drawing, and abstract as a whole.

To address the concerns about control rod accident tolerance, the materials used to construct the control rods have been improved.

Materials for reactor control rods that will remain stable to at least 1668° C. to exceed beyond design basis accident conditions and meet accident tolerant nuclear fuel conditions are described herein. Control rods constructed of several combinations of cladding and neutron absorbing materials are described. Control rods constructed of coated neutron absorbing materials are described.

Exemplary control rods may include a high temperature control rod for a nuclear fuel assembly comprising a cladding material having a melting point greater than 1500° C., and a neutron absorbing material having a melting point greater than 1500° C. wherein neither the cladding material nor the neutron absorbing material can form a eutectic with each other or with other fuel assembly materials with a melting point less than 1500° C.

Exemplary control rods may include a high temperature control rod for a nuclear fuel assembly comprising a neutron absorbing material in the form of a coated solid metal rod having a melting point greater than 1500° C. that does not form a eutectic with other materials, such as the coating material or other fuel assembly materials with a melting point less than 1500° C. The rod may be coated with the anti-oxidation coating.

An exemplary control rod for use in a nuclear fuel assembly may include a solid neutron absorbing material selected from the group consisting of Ir, Re, and Hf, and, an anti-oxidation coating on the absorbing material.

In various aspects, a combination is provided for improving the accident tolerance of a control rod in a nuclear reactor that includes a cladding material selected from the group consisting of silicon carbide, zirconium, a zirconium alloy, tungsten, a tungsten alloy, molybdenum, and a molybdenum alloy, and a neutron absorbing material.

In various aspects, the absorbing material has an effective neutron absorption cross-section equal to or greater than 8 Barns.

The cladding material may be, in certain aspects, a metal coated with an anti-oxidation coating that does not form a eutectic having a melting point less than 1500° C. The metal cladding material may be selected from the group consisting of zirconium, a zirconium alloy, tungsten, a tungsten alloy, molybdenum, and a molybdenum alloy.

The anti-oxidation coating in various aspects, may be a chromium outer coating. A niobium intermediate layer may, in certain aspects, be positioned between the outer layer and the cladding material, or between the outer layer and the solid neutron absorbing material. Molybdenum and tantalum may also be used as the intermediate layer.

A non-metal cladding material may be SiC.

In certain aspects, the absorbing material may be selected from the group consisting of $B_4C$, Re, Ir, and Hf.

The cladding may be in the form of a tube for receiving the absorbing material. The absorbing material may be in the form of one of a ceramic pellet or a metal slug housed within the tube.

BRIEF DESCRIPTION OF THE DRAWINGS

The characteristics and advantages of the present disclosure may be better understood by reference to the accompanying figure.

DESCRIPTION OF THE PREFERRED EMBODIMENTS

As used herein, the singular form of "a", "an", and "the" include the plural references unless the context clearly dictates otherwise. Thus, the articles "a" and "an" are used herein to refer to one or to more than one (i.e., to at least one) of the grammatical object of the article. By way of example, "an element" means one element or more than one element.

Directional phrases used herein, such as, for example and without limitation, top, bottom, left, right, lower, upper, front, back, and variations thereof, shall relate to the orientation of the elements shown in the accompanying drawing and are not limiting upon the claims unless otherwise expressly stated.

In the present application, including the claims, other than where otherwise indicated, all numbers expressing quantities, values or characteristics are to be understood as being modified in all instances by the term "about." Thus, numbers may be read as if preceded by the word "about" even though the term "about" may not expressly appear with the number. Accordingly, unless indicated to the contrary, any numerical parameters set forth in the following description may vary depending on the desired properties one seeks to obtain in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Further, any numerical range recited herein is intended to include all sub-ranges subsumed therein. For example, a range of "1 to 10" is intended to include any and all sub-ranges between (and including) the recited minimum value of 1 and the recited maximum value of 10, that is, having a minimum value equal to or greater than 1 and a maximum value of equal to or less than 10.

Accident tolerant nuclear fuel features claddings that can withstand much higher temperatures than the currently used zirconium (Zr) alloys. For example, SiC can withstand temperatures up to 2545° C. and coated cladding such as Cr and Nb coated Zr cladding can withstand temperatures up to 1668° C. However, to be accident tolerant, nuclear fuel components are designed for beyond design basis accidents that can result in fuel temperatures of about 1700° C. assuming the addition of a minimal amount of water. Control rods, to be accident tolerant in beyond design basis accidents, must remain stable at temperatures of at least, and preferably greater than, 1668° C.

In various aspects, materials that will provide accident tolerant reactor control rods will have an effective cross-section equal to and preferably greater than 8 Barns (1 B=$10^{-28}$ $m^2$). The effective nuclear cross-section is calculated by the weight percent of the absorber multiplied by the cross-section of its nuclear reaction multiplied by its density in grams/$cm^3$, all divided by the absorber's molecular weight in grams/gram-mole. The effective cross-section of the currently used 80% Ag/15% In/5% Cd control rods is approximately 16. The effective cross section of $Gd_2O_3$, when it is used as the absorber, is 867, based on gadolinium alone because oxygen does not play a role in absorbing neutrons.

Referring to the Figures, FIG. 1 shows a conventional fuel rod assembly 10, with a control rod assembly 12, a top nozzle 14, a bottom nozzle 16, and grid assemblies 18. The nozzles 12, 14 and the grid assemblies 18 align fuel rods 20 and control rods 22.

Figure 2:
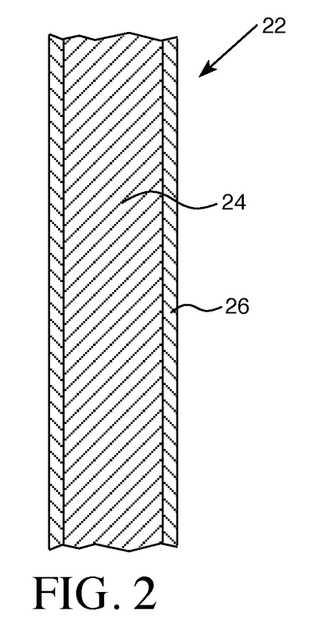
FIG. 2 is a schematic section view of an embodiment of a control rod for use in a control rod assembly such as that shown in FIG. 1.
Figure 3:
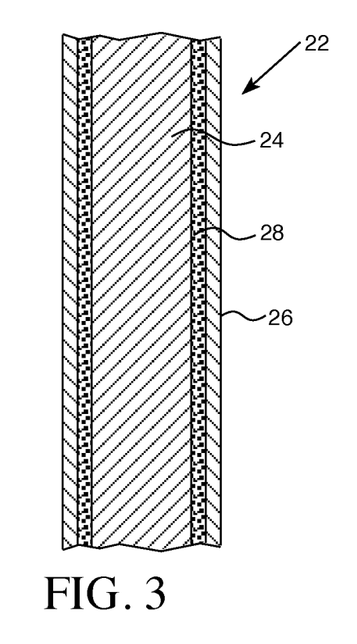
FIG. 3 is a schematic section view of an alternative embodiment of a control rod for use in a control rod assembly such as that shown in FIG. 1.

Referring to FIG. 2, a control rod 22 as described herein may include a neutron absorbing material 24 with an anti-oxidant coating 26 on the absorbing material 24. In certain aspects, as shown in FIG. 3, the neutron absorbing material 24 of control rod 22 may include an intermediate layer 28 disposed between the absorbing material 24 and an outer anti-oxidant layer 26.

Figure 4:
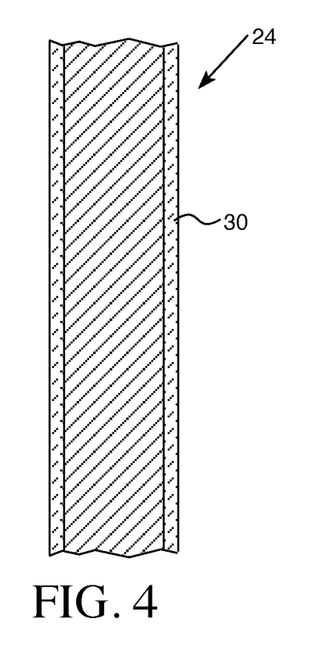
FIG. 4 is a schematic section view of an embodiment of the neutron absorbing material of the control rods shown in FIGS. 2 and 3.
Figure 5:
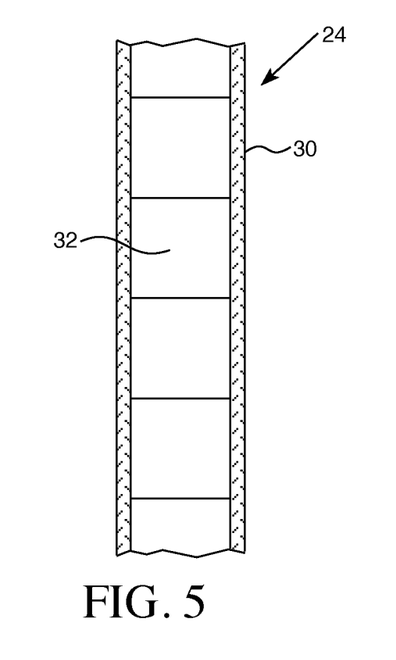
FIG. 5 is a schematic section view of an alternative embodiment of the neutron absorbing material of the control rods shown in FIGS. 2 and 3.

In certain aspects, the neutron absorbing material 24 may have a cladding layer 30, as shown in FIG. 4. The neutron absorbing material 24 may be in the form of a solid tube, as shown in FIGS. 2-4, or may be in the form of pellets or slugs 32, as shown in FIG. 5.

In various aspects, materials that will provide accident tolerant reactor control rods will have a cladding melting point of greater than 1500° C. Current modeling of nuclear reactor fuel cores with a minimal amount of water addition suggest that a temperature of approximately 1700° C. can be maintained indefinitely. Given that the control rods are approximately 200° C. cooler, cladding that can withstand temperatures greater than 1500° C. will maintain the control rod geometry.

In various aspects, the control rod neutron absorber material preferably has a melting point greater than 1500° C. With a melting point of greater than 1500° C., the absorber will not become molten in the event of a control rod cladding breach, and therefore, would not be diluted and displaced by any other molten materials.

To provide accident tolerant reactor control rods, the control rod cladding and absorber materials cannot form a eutectic (i.e., the lowest attainable melting points of the combined materials) with each other or with other fuel assembly materials to result in a melting point lower than 1500° C.

In various aspects, the control rod cladding and absorber material are designed for fluence corresponding to 20 years of operation in a combined base load/load follow/load regulation duty. Corrosion and neutron absorption over this 20 year period will not impair the operation of the control rods, a capability which is a positive aspect of the improved control rod design.

Preferably, the absorber materials will be relatively reasonably priced and fabrication costs for the control rods will not be cost prohibitive. Recognizing that the cost of materials and labor costs to fabricate the control rods may vary over time, cost factors are not a limiting factor in choice of materials for purposes of the invention, although any given material may fall into or out of favor due to market forces at any given time.

Various materials and the relevant properties of each that meet the desired specifications are set forth in Table 1. Applying the specifications above, it has been determined that in various aspects the cladding/absorber combinations and coated absorber materials listed in Table 1 meet the requirements for accident tolerant nuclear fuel assembly control rods:

TABLE I

| Absorber Material | Configuration Description | Melting Point (° C.) | Limiting Temp. (° C.) | MW | Mole % | Cross Section (B) (IAEA Hand book) | Density (gm/cm³) | Effective Cross-section (B) (Wt %* Cross-Section* density/ MW) |
|---|---|---|---|---|---|---|---|---|
| Conventional Control Tube Cladding ||||||||||
| Ag | Stainless steel tube with inner bar of absorber | | | 107.8682 | 80% | 63 | 10.5 | 4.91 |
| In | | | | 114.82 | 15% | 194 | 7.31 | 1.85 |
| Cd | | | | 112.411 | 5% | 2520 | 8.65 | 9.70 |
| Overall | | 799 | 1168 | | | | 9.93 | 16.45 |
| Improved Control Tube Material ||||||||||
| Gd₂O₃ | Gd₂O₃ pellets in Cr/Nb coated Zr tube | Gd₂O₃-2420 Gd₂O₃/ZrO₂-2200 Cr/Nb-1668 Zr/Nb-1730 Zr-1852 | 1668 | 362.498 | 87% | 48890 | 7.41 | 867 |
| Gd₂O₃ | Gd₂O₃ pellets in Cr coated Mo tube | Gd₂O₃-2420 Cr/Mo-1858 Mo-2610 | 1858 | 362.498 | 87% | 48890 | 7.41 | 867 |
| Gd₂O₃ | Gd₂O₃ pellets in Cr coated W tube | Gd₂O₃-2420 Cr/W-1863 W-3422 | 1863 | 362.498 | 87% | 48890 | 7.41 | 867 |
| Gd₂O₃ | Gd₂O₃ pellets in SiC tube | Gd₂O₃-2420 SiC-2545 | 2420 | 362.498 | 87% | 48890 | 7.41 | 867 |
| Ir | Cr/Nb coated Ir metal rod | Ir-2454 Cr/Nb-1668 Nb/Ir-1840 | 1668 | 192.22 | 100% | 425 | 22.7 | 50 |
| Ir | Ir metal slugs in SiC tube | Ir-2454 SiC-2545 | 2454 | 192.22 | 100% | 425 | 22.7 | 50 |
| B₄C | B₄C pellets in Cr/Nb coated Zr tube | B₄C-2763 Cr/Nb-1668 Zr/Nb-1730 ZrB2-1662 Zr-1852 | 1668 | 55.255 | 78% | 760 | 2.52 | 27.1 |
| B₄C | B₄C pellets in Cr coated Mo tube | B₄C-2763 Cr/Mo-1858 Mo-2610 | 1858 | 55.255 | 78% | 760 | 2.52 | 27.1 |
| B₄C | B₄C pellets in Cr coated W tube | B₄C-2763 Cr/W-1863 W-3422 | 1863 | 55.255 | 78% | 760 | 2.52 | 27.1 |

TABLE I-continued

| Absorber Material | Configuration Description | Melting Point (° C.) | Limiting Temp. (° C.) | MW | Mole % | Cross Section (B) (IAEA Hand book) | Density (gm/cm$^3$) | Effective Cross-section (B) (Wt %* Cross-Section* density/MW) |
|---|---|---|---|---|---|---|---|---|
| B$_4$C | B$_4$C pellets in SiC tube | B$_4$C-2763 SiC-2545 | 2545 | 55.255 | 78% | 760 | 2.52 | 27.1 |
| Re | Cr/Nb coated Re metal rod | Re-3180 Cr/Nb-1668 Nb/Re-2435 | 1668 | 186.207 | 100% | 89.7 | 21 | 10 |
| Re | Re slugs in SiC tube | Re-3180 SiC-2545 | 2545 | 186.207 | 100% | 89.7 | 21 | 10 |
| Hf | Cr/Nb coated Hf metal rod | Hf-2222 Cr/Nb-1668 Nb/Hf-2065 | 1668 | 178.49 | 100% | 104.1 | 13.31 | 8 |
| Hf | Hf metal slugs in SiC tube | Hf-2222 SiC-2545 | 2222 | 178.49 | 100% | 104.1 | 13.31 | 8 |
| Unacceptable Combinations with Effective Cross-Sections < 8 | | | | | | | | |
| Er$_2$O$_3$ | Er$_2$O$_3$ pellets in Cr/Nb coated Zr tube | Gd$_2$O$_3$-2344 Cr/Nb-1668 Zr/Nb-1730 Zr-1852 | 1668 | 382.518 | 87% | 159.400 | 8.64 | 3.15 |
| W | Cr/Nb coated W metal rod | W-3410 Cr/Nb-1668 Nb/W-2469 | 1668 | 183.85 | 100% | 18.4 | 19.3 | 2 |
| Os | Cr/Nb coated Os metal rod | Os-3050 Cr/Nb-1668 Nb/Os-2120 | 1668 | 190.2 | 100% | 16 | 22.6 | 2 |
| Ta | Cr/Nb coated Ta metal rod | Ta-2996 Cr/Nb-1668 Nb/Ta-2469 | 1668 | 180.9479 | 100% | 20.6 | 16.5 | 2 |
| Nb | Cr coated Nb metal rod | Nb-2468 Cr/Nb-1668 | 1668 | 92.90638 | 100% | 1.15 | 8.57 | 0.106 |

In various aspects, exemplary cladding materials used in the combination for control rods may include the following:

1. Zirconium (Zr) alloy cladding with an outer coating of chromium (Cr) and an intermediate layer of niobium (Nb), between the Cr and the Zr layers. For this cladding, the lowest melting eutectic is between Cr and Nb at 1668° C.

2. Tungsten (W) alloy cladding with an outer coating of Cr. For this cladding, the lowest melting eutectic is 1863° C.

3. Molybdenum (Mo) alloy cladding with an outer coating of Cr. For this cladding, the lowest melting eutectic is 1858° C.

4. Silicon carbide (SiC) cladding. The decomposition temperature is about 2545° C.

In various aspects, the zirconium alloy may be coated ZIRLO™, made in accordance with the procedures disclosed in U.S. Pat. No. 4,649,023, incorporated in relevant part herein by reference. ZIRLO™ is an alloy comprising, by weight percent, 0.5-2.0 niobium, 0.7-1.5 tin, 0.07-0.14 iron, and 0.03-0.14 of at least one of nickel and chromium, and at least 0.12 total of iron, nickel and chromium, and up to 220 ppm C, and the balance essentially zirconium. Preferably, the alloy contains 0.03-008 chromium, and 0.03-0.08 nickel. Those skilled in the art will appreciate that other zirconium alloys may be acceptable for use in a desired application.

In various aspects, exemplary absorber materials used for control rods may include the following:

1. $Gd_2O_3$ has a melting point of 2420° C. and a very high neutron absorptivity. The relatively high cost of $Gd_2O_3$ makes this material less than ideal at this time if used alone. However, because of its very high thermal cross-section, it may be diluted up to, or by about, a factor of 50 with other high melting point, inexpensive oxides such as $Al_2O_3$ (melting point 2072° C.) or CaO (2575° C. melting point), to lower the ultimate cost.

2. $B_4C$ has a high melting point of 2763° C. and a reasonably high neutron absorptivity. Unlike $Gd_2O_3$, it is not cost prohibitive. In certain aspects, $B_4C$ may be a useful absorber.

3. Rhenium (Re) has a melting point of 3180° C. and a moderate neutron absorptivity. It is also relatively expensive. In certain aspects, however, Re may be a useful absorber.

4. Hafnium (Hf) has a melting point of 2222° C. and a moderate neutron absorptivity. It is also relatively expensive. In certain aspects, however, Hf may be a useful absorber. Other metal absorber materials shown in Table 1 include osmium (Os), tantalum (Ta), and niobium (Nb), but the effective cross-sectional area of these materials is less than 8 Barns so they are not preferred for use in nuclear fuel assemblies to meet beyond design basis accident tolerance specifications.

The absorbers may be in the form of pellets or slugs inserted into hollow cladding tubes. Slugs, as used herein, refers to the metal absorbers, and pellets, as used herein, refers to pressed and sintered ceramic absorbers. Absorber material formed into pellets as listed in Table 1 may include $Gd_2O_3$ and $B_4C$. Absorber material formed into slugs as listed in Table 1, may include iridium (Ir), rhenium (Re), and hafnium (Hf). Whether a slug or pellets absorber is used, the geometry is generally the same, the object being to fit within the hollow of a cladding tube. They may be cylindrical or any other suitable shape, such as square or rectangular blocks, depending on the shape of the hollow cavity in the cladding tube. There may be a single absorber or may be a plurality of absorbers in the form of stacked cylinders or stacked blocks.

The absorbers may be in the form of a solid metal rod having a coating material over the rod. For example, referring to Table 1, absorber metals, such as Ir, Re, and Hf, may be in the configuration of a solid rod. The coating material overlaying the rod may comprise a Cr outer coating with or without an intermediate coating layer of Nb to protect the underlying metal rod from oxidation during normal operating and accident conditions. Molybdenum and tantalum may also be used as the intermediate layer. In this embodiment, there is no cladding material.

A high temperature control rod may comprise, for example, a metal or metal alloy cladding material having a melting point greater than 1500° C. and an anti-oxidation coating for these metals that does not form a eutectic that has a melting point that is less than 1500° C. The control rod has a high neutron absorption cross-section. Another exemplary high temperature control rod may comprise SiC and a neutron absorbing material with a melting point greater than 1500° C. which does not form a eutectic that has a melting point less than 1500° C. This embodiment of the control rod also has a high neutron absorption cross-section.

The metal cladding material may be selected from zirconium (Zr), tungsten (W), and molybdenum (Mo), and alloys thereof. The alloys may be selected from any suitable alloys for use in the high temperature environments of a nuclear reactor known to those skilled in the art. In various aspects, the cladding material may be in the form of a tube configured to hold absorber pellets or slugs.

In various aspects, the cladding tubes may be coated with an anti-oxidation material. The coating material may comprise a chromium (Cr) outer coating with or without an inner coating of niobium (Nb). Other coating combinations may be used. For example, a Cr outer layer with either a Mo or a Ta intermediate layer may be selected.

These control rod cladding and neutron absorbing material combinations offer cost effective, relatively easy to manufacture combinations to enhance the accident tolerance of a nuclear fuel assembly.

The tubes, rods and metal slugs described herein may be machined by any method known to those skilled in the art. Because of the close tolerances for size, configuration, molecular weight and other properties identified, for example, in Table 1 and those known to be relevant in the nuclear industry, precision manufacturing methods should be used.

Pellets may be formed by known methods of manufacturing pellets in other commercial contexts. For example, the ceramic absorber materials in powder, or particulate form, may be formed into a pellet by first homogenizing the particles to ensure relative uniformity in terms of particle size distribution and surface area. In certain aspects, additives, such as lubricants, burnable absorbers and pore-forming agents may be added. The particles may be formed into pellets by compressing the mixture of particles in suitable commercially available mechanical or hydraulic presses to achieve the desired "green" density and strength.

A basic press may incorporate a die platen with single action capability while the most complex styles have multiple moving platens to form "multi-level" parts. Presses are available in a wide range of tonnage capability. The tonnage required to press powder into the desired compact pellet shape is determined by multiplying the projected surface area of the part by a load factor determined by the compressibility characteristics of the powder.

To begin the process, the mixture of particles is filled into a die. The rate of die filling is based largely on the flowability of the particles.

Once the die is filled, a punch moves towards the particles. The punch applies pressure to the particles, compacting them to the geometry of the die. In certain pelletizing processes, the particles may be fed into a die and pressed biaxially into cylindrical pellets using a load of several hundred MPa.

Following compression, the pellets are sintered by heating in a furnace at temperatures varying with the material being sintered under a controlled atmosphere, usually comprised of argon. Sintering is a thermal process that consolidates the green pellets by converting the mechanical bonds of the particles formed during compression into stronger bonds and greatly strengthened pellets. The compressed and sintered pellets are then cooled and machined to the desired dimensions. Exemplary pellets may be about one centimeter, or slightly less, in diameter, and one centimeter, or slightly more, in length.

The anti-oxidation coating may be applied using a thermal deposition process, such as a cold spray process. Where there are two layers, the inner layer will be deposited first and may be ground and polished before deposition of the outer layer, which can be ground and polished thereafter.

A cold spray method may proceed by delivering a carrier gas to a heater where the carrier gas is heated to a temperature sufficient to maintain the gas at a desired temperature, for example, from 100° C. to 500° C., after expansion of the gas as it passes through a nozzle. In various aspects, the carrier gas may be pre-heated to a temperature between 200° C. and 1200° C., with a pressure, for example, of 5.0 MPa. In certain aspects, the carrier gas may be pre-heated to a temperature between 200° C. and 1000° C., or in certain aspects, 300° C. and 900° C. and in other aspects, between 500° C. and 800° C. The temperature will depend on the Joule-Thomson cooling coefficient of the particular gas used as the carrier. Whether or not a gas cools upon expansion or compression when subjected to pressure changes depends on the value of its Joule-Thomson coefficient. For positive Joule-Thomson coefficients, the carrier gas cools and must be preheated to prevent excessive cooling which can affect the performance of the cold spray process. Those skilled in the art can determine the degree of heating using well known calculations to prevent excessive cooling. See, for example, for $N_2$ as a carrier gas, if the inlet temperature is 130° C., the Joule-Thomson coefficient is 0.1° C./bar. For the gas to impact the tube at 130° C. if its initial pressure is 10 bar (~146.9 psia) and the final pressure is 1 bar (~14.69 psia), then the gas needs to be preheated to about 9 bar*0.1° C./bar or about 0.9 C to about 130.9° C.

For example, the temperature for helium gas as the carrier is preferably 450° C. at a pressure of 3.0 to 4.0 MPa, and the temperature for nitrogen as the carrier may be 1100° C. at a pressure of 5.0 MPa, but may also be 600° C.-800° C. at a pressure of 3.0 to 4.0 MPa. Those skilled in the art will recognize that the temperature and pressure variables may change depending on the type of the equipment used and that equipment can be modified to adjust the temperature, pressure and volume parameters.

Suitable carrier gases are those that are inert or are not reactive, and those that particularly will not react with the Cr or Nb particles or the tube or rod substrate to be coated. Exemplary carrier gases include nitrogen ($N_2$), hydrogen ($H_2$), argon (Ar), carbon dioxide ($CO_2$), and helium (He).

There is considerable flexibility in regard to the selected carrier gases. Mixtures of gases may be used. Selection is driven by both physics and economics. For example, lower molecular weight gases provide higher velocities, but the highest velocities should be avoided as they could lead to a rebound of particles and therefore diminish the number of deposited particles.

In an exemplary cold spray process, a high pressure gas enters through a conduit to a heater, where heating occurs quickly; substantially instantaneously. When heated to the desired temperature, the gas is directed to a gun-like instrument. Particles of the desired coating material, in this case, Cr or Nb are held in a hopper, and are released and directed to the gun where they are forced through a nozzle towards the rod or tube substrate by a pressurized gas jet. The sprayed Cr or Nb particles are deposited onto rod or tube surface to form a coating comprised of the particles The cold spray process relies on the controlled expansion of the heated carrier gas to propel the particles onto the tube or rod substrate. The particles impact the substrate or a previous deposited layer and undergo plastic deformation through adiabatic shear. Subsequent particle impacts build up to form the coating. The particles may also be warmed to temperatures one-third to one-half the melting point of powder expressed in degrees Kelvin before entering the flowing carrier gas in order to promote deformation. The nozzle is rastered (i.e., sprayed in a pattern in which an area is sprayed from side to side in lines from top to bottom) across the area to be coated or where material buildup is needed.

The tube or rod may require some surface preparation such as grinding or chemical cleaning to remove surface contamination to improve adherence and distribution of the coating.

The particles are sprayed at a velocity sufficient to provide a compact, impervious, or substantially impervious, coating layers. In various aspects the velocity of the jet spray may be from 800 to 4000 ft./sec. (about 243.84 to 1219.20 meters/sec.). The Cr or Nb particles are deposited onto the surface of the tube or rod at a rate sufficient to provide the desired production rate, at a commercial or research level.

Those skilled in the art can readily calculate the rate of deposition based on the equipment used in the process, and can adjust the rate of deposition by altering the components that factor into the rate. In certain aspects of the method, the rate of particle deposition may be up to 1000 kg/hour. An acceptable rate is between 1 and 100 kg/hour, and in various aspects, may be between 10 and 100 kg/hour, but higher and lower rates, for example, 1.5 kg/hour, have been successfully used.

Following the deposition of the coating, the method may further include annealing the coating. Annealing modifies mechanical properties and microstructure of the coated tube. Annealing involves heating the coating in the temperature range of 200° C. to 800° C. but preferably between 350° C. to 550° C.

The coated substrate may also be ground, buffed, polished, or otherwise further processed following the coating or annealing steps by any of a variety of known means to achieve a smoother surface finish.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

All patents, patent applications, publications, or other disclosure material mentioned herein, are hereby incorporated by reference in their entirety as if each individual reference was expressly incorporated by reference respectively. All references, and any material, or portion thereof, that are said to be incorporated by reference herein are incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference and the disclosure expressly set forth in the present application controls.

The present invention has been described with reference to various exemplary and illustrative embodiments. The embodiments described herein are understood as providing illustrative features of varying detail of various embodiments of the disclosed invention; and therefore, unless otherwise specified, it is to be understood that, to the extent possible, one or more features, elements, components, constituents, ingredients, structures, modules, and/or aspects of the disclosed embodiments may be combined, separated, interchanged, and/or rearranged with or relative to one or more other features, elements, components, constituents, ingredients, structures, modules, and/or aspects of the disclosed embodiments without departing from the scope of the disclosed invention. Accordingly, it will be recognized by persons having ordinary skill in the art that various substitutions, modifications or combinations of any of the exemplary embodiments may be made without departing from the scope of the invention. In addition, persons skilled in the art will recognize, or be able to ascertain using no more than routine experimentation, many equivalents to the various embodiments of the invention described herein upon review of this specification. Thus, the invention is not limited by the description of the various embodiments, but rather by the claims.

What is claimed is:

1. A control rod for a nuclear fuel assembly comprising:
    a cladding material having a melting point greater than 1500° C.; and
    a neutron absorbing material having a melting point greater than 1500° C.; and
    an intermediate layer coated on the cladding material,
        wherein the intermediate layer is intermediate the cladding material and an outer coating,
        wherein the intermediate layer is selected from the group consisting of niobium, molybdenum, and tantalum,
    wherein the cladding and the absorbing materials do not form a eutectic that has a melting point less than 1500° C., and
    wherein the cladding material and the intermediate layer do not form a eutectic that has a melting point less than 1500° C.

2. The control rod recited in claim 1 wherein the cladding material is silicon carbide.

3. The control rod recited in claim 1
    wherein the cladding material is a metal,
    wherein the outer coating is an anti-oxidation coating on the intermediate layer,
    the cladding material and the anti-oxidation coating do not form a eutectic that has a melting point less than 1500° C.

4. The control rod recited in claim 3 wherein the anti-oxidation coating comprises a chromium outer coating.

5. The control rod recited in claim 4 wherein the intermediate layer is positioned between the chromium outer coating and the cladding material.

6. The control rod recited in claim 1 wherein the cladding material is selected from the group consisting of zirconium, tungsten, molybdenum, and alloys of each.

7. The control rod recited in claim 1 wherein the neutron absorbing material has an effective neutron absorption cross-section equal to or greater than 8 Barns.

8. The control rod recited in claim 1 wherein the absorbing material is $Gd_2O_3$.

9. The control rod recited in claim 8 wherein the $Gd_2O_3$ is diluted with an oxide.

10. The control rod recited in claim 9 wherein the oxide is one of $Al_2O_3$ or CaO.

11. The control rod recited in claim 1 wherein the neutron absorbing material is selected from the group consisting of $B_4C$, Re, Ir, and Hf.

12. A control rod for a nuclear fuel assembly, the control rod comprising:
    a cladding material having a melting point greater than 1500° C.; and
    a neutron absorbing material having a melting point greater than 1500° C.,
    wherein the cladding and absorbing materials do not form a eutectic that has a melting point less than 1500° C.,
    wherein the cladding material is a metal coated with an anti-oxidation coating, the anti-oxidation coating and the cladding material do not form a eutectic that has a melting point less than 1500° C., and
    wherein the anti-oxidation coating comprises a chromium outer coating and an intermediate layer, the intermediate layer is positioned between the chromium outer coating and the cladding material, and the intermediate layer is selected from the group consisting of niobium, molybdenum, and tantalum.

13. A control rod for a nuclear fuel assembly, the control rod comprising:
    a cladding material having a melting point greater than 1500° C.;
    a neutron absorbing material having a melting point greater than 1500° C.; and
    an anti-oxidation coating coated on the cladding material,
    wherein the anti-oxidation coating comprises a chromium outer coating and an intermediate layer, the intermediate layer is positioned between the chromium outer coating and the cladding material, and the intermediate layer is selected from the group consisting of niobium, molybdenum, and tantalum,
    wherein the cladding and absorbing materials do not form a eutectic that has a melting point less than 1500° C., and
    wherein the anti-oxidation coating and the cladding material do not form a eutectic that has a melting point less than 1500° C.

* * * * *